United States Patent [19]

Fishman

[11] Patent Number: 5,240,615
[45] Date of Patent: Aug. 31, 1993

[54] COMPOSITE MEMBRANE COMPOSED OF MICROPOROUS POLYVINYLIDENE DIFLUORIDE MEMBRANE LAMINATED TO POROUS SUPPORT AND PROCESS FOR ITS PREPARATION

[76] Inventor: Jerry H. Fishman, 227 Central Park West, New York, N.Y. 10024

[21] Appl. No.: 747,852

[22] Filed: Aug. 20, 1991

[51] Int. Cl.$^5$ .............................................. B01D 71/34
[52] U.S. Cl. ................................. 210/651; 210/500.42
[58] Field of Search ............... 210/490, 651, 652, 653, 210/654, 500.42; 427/245, 246; 55/16, 158

[56] References Cited

U.S. PATENT DOCUMENTS

| | | | |
|---|---|---|---|
| 3,615,024 | 10/1971 | Michaels | 210/500.42 X |
| 4,203,847 | 5/1980 | Grandine et al. | 210/500.42 X |
| 4,776,959 | 10/1988 | Kasai et al. | 210/500.42 X |
| 4,824,568 | 4/1989 | Allegrezza, Jr. et al. | 210/500.42 X |
| 5,017,292 | 5/1991 | DiLeo et al. | 210/500.36 X |

Primary Examiner—Frank Spear
Attorney, Agent, or Firm—Bernard Lieberman

[57] ABSTRACT

A smooth microporous polyvinylidene difluoride membrane laminated to a porous support is prepared without glues or binders by gelling in aqueous media a layer of a solution of polyvinylidene difluoride upon the porous support. The polyvinylidene difluoride surface of the composite microporous laminated membranes has discrete pore openings with diameters less than 0.2 $\mu$m and especially less than 0.12 $\mu$m where the density of pore openings with diameters greater than 0.01 $\mu$m is at least $1 \times 10^5$ pores/cm$^2$ but especially greater than $1 \times 10^8$ pores/cm$^2$. These membranes can be used, for example, in filtration or collection of one or more dissolved or suspended substances from a liquid medium.

31 Claims, 2 Drawing Sheets

COMPOSITE MEMBRANE COMPOSED OF MICROPOROUS POLYVINYLIDENE DIFLUORIDE MEMBRANE LAMINATED TO POROUS SUPPORT AND PROCESS FOR ITS PREPARATION

BACKGROUND OF THE INVENTION

1. Field of the Invention

This invention relates to a microporous, polyvinylidene difluoride (PVDF) membrane. More specifically, the invention relates to a microporous PVDF/support composite membrane and to the method for preparing such membrane. In particular, the invention relates to a microporous PVDF membrane which is laminated by a phase-inversion process to another porous membrane without the use of glue or binders, such that the exposed surface of the PVDF membrane is smooth and contains a multiplicity of discrete pore openings, having submicron diameters.

2. Description of the Prior Art

Microporous membranes are commonly used to separate components from a solution, to remove particulates from a liquid or gaseous medium or to transmit substances in a controlled manner. Such membranes find a variety of applications in diverse areas of technology, including, for example, recovery of electroplating metals, blood dialysis, maintenance of cell cultures, food processing, biosensors, sensing electrodes, purification of bioprocessing products, separators for battery compartments, sterilization of solutions, blood plasma processing by electrodialysis, artificial organ construction, protein separation, purification of natural flavors and fragrances, devices for controlled release of drugs, industrial waste treatment and uses in various other areas of technology. The wide variety of processes and conditions in which microporous membranes are used indicates a need for membranes with a wide range of physical, chemical and structural features.

The PVDF polymer has features, in addition to its very good membrane forming ability, that can accommodate a wide variety of operating conditions due to its chemical and biological inertness. Also, PVDF membranes are structurally useful at temperatures ranging from at least $-150°$ C. to $140°$ C. Also, PVDF is nontoxic. Thus, PVDF is an outstanding material for microporous filtration or barrier membranes.

One of the most useful and common methods of forming microporous membranes from organic polymers is the phaseinversion method. In the case of PVDF, the application of the phase inversion procedure is complicated by the tendency of the gel to shrink and distort in the course of its formation and then to shrink and distort further upon drying to form a membrane.

Shrinkage and distortion of PVDF membranes can be controlled by physically restraining the gel during formation, however, physical restraint of shrinkage is technically complicated. Shrinkage is particularly problematic when, as required within this invention, a highly aqueous gelling medium is used, resulting in a distorted, shrivelled structure rather than a smooth, undisturbed membrane. Several phase inversion methods for producing undistorted microporous PVDF membranes without the need to restrain the gel are known, however, membranes formed by these methods have non-discrete pore openings embedded in a disturbed, sponge-like surface structure.

U.S. Pat. No. 3,642,668 to Bailey, et al. describes the use of alcohol as a gelling medium in a phase-inversion procedure to form PVDF membranes. In alcohol, shrinkage is greatly reduced, hence there is no need to physically restrain the gel during formation and sheets of PVDF membrane can be formed by extrusion of the PVDF solution through a slotted die directly into a methanol gelling bath.

In U.S. Pat. No. 4,203,848 to Grandine, acetone is used as a gelling medium. Mixtures of acetone and water, containing at least 50% acetone are used to prevent gel shrinkage during formation of a non-supported PVDF membrane.

U.S. Pat. No. 4,806,291 to Susa also discloses the use of alcohol as a gelation medium wherein the PVDF casting solution includes ammonia salts as pore-forming agents. The PVDF solution is cast upon a glass plate or upon a fibrous or porous supporting structure.

U.S. Pat. No. 4,384,047 to Benzinger describes a phase-inversion method for non-supported PVDF membrane formation where restraint during gel formation is unnecessary in order to obtain smooth, wrinkle-free membranes. Triethylphosphate is the solvent used for the PVDF and inclusion is required of any of the nonsolvents glycerol, ethylene glycol or phosphoric acid to act as pore-forming agents. Gelation is achieved in ice water.

In British Patent 1,212,758, to Amicon Corp., water is listed as a convenient gelling agent and PVDF is listed as candidate material for phase-inversion membranes but no examples are given for forming these PVDF membranes and moreover, no consideration is given to the problems of severe shrinkage when PVDF membranes are fabricated in aqueous gelling media.

The membranes produced by the several above-mentioned methods are flat, unwrinkled and uniform. However, scanning electron microscopy shows that the pore openings are non-discrete and the surface structure of the membrane is sponge-like. The spongy surface tends to trap and retain material when the membrane is used in filtration operations and thus the methane eventually becomes clogged with little prospect of clearing the entrapped material from the membrane matrix.

Polyvinylidene membranes of the present invention, by contrast, have discrete, undistorted pore openings in an undisturbed smooth surface. To achieve this, the phase inversion process is conducted in aqueous media and the PVDF layer is firmly anchored during its formation to the surface of the prefabricated microporous support. This not only prevents shrinkage and distortion of the PVDF layer in the course of its formation but strengthens the final membrane. Surprisingly, this lamination process occurs without adhesives, bonding agents or chemical reaction.

Lamination of membranes in series i.e., with surface-to-surface contact, has been widely used to reinforce fragile, thin membranes. In particular, lamination of membranes has been used to provide support for reverse osmosis (RO) membranes which must necessarily be thin in order to function efficiently but must also be able to withstand pressures of 100–800 psi. The most widely used support for these thin membranes are microporous polysulfone membranes having an average pore diameter of at least 0.1 $\mu$m, although a variety of materials have been used to support such membranes, as disclosed in U.S. Pat. No. 4,848,700 to Fibiger, et al. For example, in U.S. Pat. No. 4,260,652, it is suggested that microporous PVDF membranes may serve as support structures for reverse osmosis membranes. Reverse osmosis membranes are generally characterized by pore sizes of less than 0.01 μm.

It is accordingly an object of the present invention to provide a microporous PVDF series laminated composite membrane having discrete pore openings in an undistorted PVDF surface and which is useful in a wide variety of processes and under a variety of conditions.

It is another object of the present invention to provide a microporous PVDF composite membrane impregnated with a hydrophilic agent to adjust the hydrophobic/hydrophilic characteristics of the membrane.

Another object of the present invention is to provide a microporous PVDF composite membrane impregnated with specific concentrations of poly(2-hydroxyethyl methacrylate) (PHEMA) resulting in an alteration of the hydrophobicity/hydrophilicity of the membrane and an alteration in the permeability properties of the membrane.

It is another object of the present invention to provide a microporous composite PVDF membrane having a multiplicity of discrete pore openings at the exposed PVDF surface in the range of greater than 0.01 μm up to about 0.2 μm in diameter and which includes at least two membranes laminated in series wherein at least one membrane is comprised of polyvinylidene difluoride and an adjacent membrane is a supporting membrane.

A further object of the present invention is to provide a microporous composite PVDF membrane impregnated with a specific concentration of PHEMA such that the permeability properties of the membrane reflect those of PHEMA.

Still yet another object of the invention is to provide a composite microporous PVDF supported membrane useful for separating one component or group of components from a mixture of components in an aqueous or nonaqueous medium.

It is also an object of the invention to provide a composite microporous PVDF supported membrane which can be used to separate microorganisms or proteinaceous substances from a solution or suspension thereof.

A still further object of the invention is to provide a simple and economical process for preparing the aforesaid microporous PVDF supported composite membrane having discrete pore openings in the PVDF surface.

SUMMARY OF THE INVENTION

The above and other objects of the invention which will become more readily apparent from the following detailed description and accompanying drawings are provided, in the first instance, by a microporous composite membrane which comprises at least two layers laminated in series wherein at least one of the layers comprises at least 90% polyvinylidene difluoride and an adjacent layer is a porous support and the exposed surface of the polyvinylidene difluoride layer of the membrane has discrete pore openings, wherein at least 90% of pore openings have diameters smaller than 0.2 μm and preferably smaller than 0.12 μm. In the diameter range of from about 0.01 μm to 0.2 μm the pore opening density is at least $1 \times 10^5$ pores/cm$^2$, and preferably at least $1 \times 10^8$ pores/cm$^2$.

The composite membranes of the present invention can be prepared by casting an organic solvent solution of polyvinylidene difluoride (PVDF) onto the surface of a porous support to form a PVDF-solvent layer, contacting the PVDF-solvent layer with an aqueous medium to form a gel on the support and drying to form the composite membrane. The product membranes are uniform in appearance, without kinks or structural distortions.

In a further aspect, the membranes of the present invention further include a hydrophilic agent impregnated in the pores of the PVDF layer. The membranes according to this embodiment may be prepared by immersing the dried, microporous composite membrane in an impregnating solution of a hydrophilic agent, air drying to evaporate the solvent or immediately immersing in water to precipitate the hydrophilic agent whereby the hydrophilic agent becomes impregnated in the pores of the PVDF layer of the membrane.

The present invention also provides a process for separating at least one component from a mixture of components in a liquid medium. A liquid medium containing a mixture of components is brought into contact with the polyvinylidene difluoride side of the microporous composite membrane under conditions such that, for example, a higher pressure is applied to the PVDF surface of the membrane than to the support surface whereby liquid medium containing at least one component is passed through the membrane. Alternatively, an electric current can be used as the driving force. The microporous PVDF composite membrane is also useful in a process for filtering particulate matter wherein a liquid or gaseous medium containing particulate matter is brought into contact with the PVDF surface of the composite membrane under a higher pressure than is applied to the support side of the composite membrane, whereby the medium passes through the membrane and particulate matter is collected on the PVDF surface.

Figure 1:
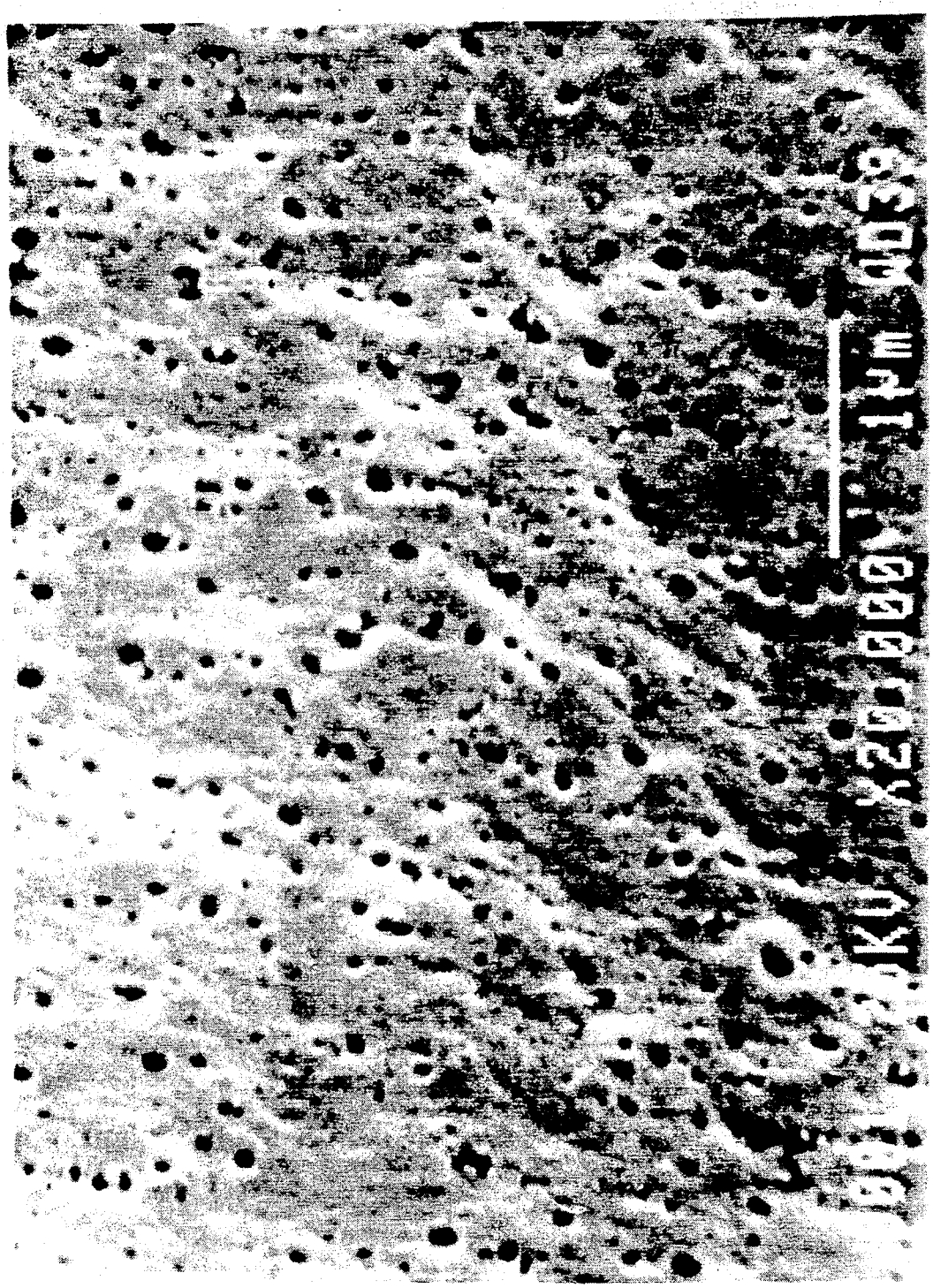
FIG. 1 is a scanning electron micrograph of the PVDF surface of a microporous membrane made by the process of the present invention (Example 6) in which an organic solvent solution of polyvinylidene difluoride was cast upon a supporting membrane and gelled in aqueous media and dried. Magnification is 20,000×.

The size of the resulting pore openings is indicated by comparison to the 1 μm scale at the base of each micrograph.

DETAILED DESCRIPTION OF THE INVENTION

The microporous polyvinylidene difluoride (PVDF) membranes of the present invention are laminated, without the use of glues or binders, to other porous membranes, composed of, for example, natural polymers, synthetic polymers, metals, metal alloys, glass, ceramics or blends of such materials. The exposed surface of the PVDF membrane is smooth and has a multiplicity of discrete pore openings of sub-micron diameter. The PVDF layer is firmly and directly adhered to the porous support.

The fabrication of the microporous PVDF membranes of the present invention is based upon phase-inversion technology, one of the oldest known methods of fabricating microporous membranes from organic polymers. Basically, phase-inversion involves the casting of a polymer solution onto a support structure and gelling of the polymer by immersion of the supported solution film into a nonsolvent which is miscible with the polymer solvent. As a result of more rapid desolvation of the polymer at the interface with the nonsolvent than in the protected interior of the nascent membrane, the pores show some degree of asymmetry. Generally, the pore opening diameter at the outer surface of the membrane is smaller than in the interior and at the internal surface (interface) with the support structure.

These differences are particularly pronounced when the gelling non-solvent is aqueous. In this case the pore openings at the outer surface are not only smaller than those obtained with organic gelling media but are also discrete, i.e. they are clearly separated one from another, and the PVDF surface in which they are located appears as a continuous undisturbed structure, while the pores within the membrane, however, are part of a tortuous structure with the pore diameter very much larger than the diameter of the pore openings at the surface.

By contrast, when organic gelling media are used the outer surface of the formed PVDF membrane, examined by scanning electron microscopy (SEM), appears sponge-like and the pore openings are not distinct, but rather, they reflect more the tortuous pore structure seen within the membrane.

The features of the pore openings of PVDF membranes obtained with aqueous gelling media make them far more useful in all manner (microporous membrane) applications than the PVDF membranes obtained with organic gelling media.

PVDF membranes tend to shrink in the course of fabrication by the phase inversion method. This shrinking tendency is so severe when aqueous gelling media are used that, unless the nascent membranes are properly anchored during gelling and preferably also during subsequent drying, they shrink to a distorted useless structure.

Anchoring to produce a uniform and reproducible PVDF membrane with the desired surface and pore opening features is technically difficult, and this invention overcomes this difficulty.

In the present invention, microporous PVDF membranes having an undisturbed exposed surface with a multiplicity of discrete pore openings in the range of from at least about 0.01 $\mu$m and up to about 0.2 $\mu$m diameter, for example, 0.05, 0.08, 0.10, 0, 0.12, 0.16, 0.18, 0.20 $\mu$m diameter, are formed by a phase-inversion method in which a layer of the PVDF polymer solution is gelled in an aqueous medium under conditions in which shrinking of the gel is prevented. In the context of the present invention, aqueous gelling media include water, as well as, solutions of water-soluble inorganic or organic salts in water or solutions of organic solvents in water at a concentration of organic solvent below which a gross transition from a smooth to spongy outer membrane surface occurs. Generally, amounts of organic solvents such as lower alcohols, e.g., methanol, ethanol, propanol; aldehydes, e.g. formaldehyde; organic acid esters, e.g., ethylacetate, and the like, in amounts up to about 35%, preferably up to about 30% by weight, especially up to 20%, can be used without forming a spongy outer surface. However, for any particular organic solvent the acceptable amount can be easily determined by routine experimentation.

The PVDF phase-inversion gel of the present invention is formed on a finely porous support whereby it is firmly anchored to the support surface and so prevented from shrinking. The surprising ability of finely porous supports to anchor the nascent PVDF gel layer is a key feature of this invention. In the product membrane the exposed fine surface of the PVDF layer is microporous, uniform and reproducible. Furthermore, a PVDF membrane in a composite structure according to the present invention, can be made much thinner than an unsupported PVDF membrane since the laminate structure provides the membrane with physical strength.

A possible explanation for the laminating effect is that upon first contact with the aqueous gelling medium an initial skin forms at the interface between the PVDF solution layer and the gelling medium and as the gel skin attempts to shrink it exerts strong pressure on the underlying polymer solution forcing part of it into the pore openings of the support layer. Water continues desolvating the PVDF polymer and eventually gels the polymer within the pores of the support in the interface zone, anchoring the PVDF firmly to the support. The flat support must be sufficiently rigid or rigidly held so that shrinking forces of the gelling PVDF should not cause the support layer to fold and become distorted.

The general method of making the laminate composite PVDF membranes of the present invention is to spread the PVDF solution onto a porous support and immediately or after the solvent has partly evaporated, contacting the layer of PVDF solution with the aqueous gelling medium. When the PVDF solvent is sufficiently diffused away, the composite is withdrawn from the gelling medium, dried at ambient temperature and optionally, annealed for one or more minutes, such as 1 to 30 minutes, preferably 2 to 20 minutes, at 70-100° C., for example, in an air oven or in water.

Figure 2:
FIG. 2 is an electron micrograph of the PVDF surface of a microporous membrane made by a process (Comparative Example 1) in which an organic solvent solution of polyvinylidene difluoride was cast upon a supporting membrane and gelled in methanol and dried. Magnification is 20,000×.

FIG. 1 is an electron micrograph of a microporous membrane made by such a process. Discrete pore openings having submicron diameters can be seen. In contrast, FIG. 2 is an electron micrograph of a porous membrane made by a process, wherein the polyvinylidene difluoride solution which had been cast upon a support membrane was gelled by contact with methanol. The surface is spongy, having large, nondiscrete interconnecting openings to a tortuous network-like pore structure.

The membrane produced by the method of the present invention is usable without annealing. Annealing, however, serves to increase the dimensional stability, chemical inertness and tear strength of the PVDF layer of the laminate membrane.

The porous support layer may be flexible, rigid, or semi-rigid, and is preferably self-supporting and microporous. Suitable materials for the support layer include, for example, natural polymers, synthetic polymers, carbon, metals, metal alloys, ceramics, glass or mixtures thereof. Strong microporous laminated PVDF composite membranes can be made using a variety of commercially available membranes as support structures. Such membranes include, for example, polytetrafluoroethylene (PTFE) membranes (such as those available from M.L. Gore and Associates, Inc., Elkton, MD), nylon membranes (Pall BioSupport, Glen Cove, NY), paper filters (such as those available from Schleicher & Schuell, Keene, NH, and Whatman, Clifton, NJ), glass filters (such as those available from Whatman, Clifton, NJ), symmetric and asymmetric polysulfone membranes (such as those available from Hoechst Celanese, Charlotte, NC; Brunswick Technetics, San Diego, CA), polypropylene membranes (such as those available from Hoechst Celanese, Charlotte, NC; Pall BioSupport, Glen Cove, NY) and various other types of membranes. Preferably, the diameters of the pores on the surface of the support layer for anchoring the PVDF as a laminate are in the range of from about 0.1 µm to about 2.0 µm. However, pore diameters in the range of from about 0.01 µm to about 25 µm are suitable, depending on end use application.

The solvent for the polyvinylidene difluoride solution which is cast upon the support can be any solvent which is miscible with water or with an aqueous solution. Preferred PVDF solvents include, for example, dimethylformamide (DMF), dimethylacetamide (DMAA), diethylacetamide (DEAA) or dimethylsulfoxide (DMSO) or mixtures of these solvents with each other or with any other solvent useful with PVDF. An especially preferred solvent is dimethylacetamide.

It is not necessary that the support be fully chemically inert to the PVDF solvent since contact with the PVDF solution can be made at a low temperature or for a very short period by immediately immersing the solution covered support in the aqueous gelling medium.

The aqueous medium used to gel the PVDF solution upon the support can be water, aqueous solutions of inorganic salts such as, for example sodium chloride, or aqueous solutions of organic salts such as, for example, sodium citrate or mixtures of such salt solutions. When aqueous solutions of organic solvents such as isopropanol, for example, are used as gelling media (with or without salts), the weight ratio of water to water-soluble organic solvents in the aqueous medium is preferably greater than 1.85:1. As described previously, however, water is the preferred aqueous medium.

The microporous membrane of the present invention contains one or both surface layers comprised of at least 90% polyvinylidene difluoride. Laminated membranes may be prepared using blends of vinylidene difluoride homopolymer and copolymer(s) such that one surface layer comprises at least 90% vinylidene difluoride. Typical monomers that copolymerize with vinylidene difluoride may include ethylenically unsaturated monomers having the >C=C< group, preferably without other functional groups. Examples of such comonomers include olefins, such as ethylene, propylene, 1-butene, vinyl halide monomers, such as vinyl chloride, vinyl fluoride, vinyl bromide, vinylidene chloride, vinylidene fluoride; carboxylic acid esters, such as, ethyl acrylate, methyl methacrylate, vinyl acetate; and other vinyl monomers, such as, vinyl pyrrolidone, and the like. Accordingly, unless the context indicates otherwise, the term polyvinylidene difluoride is intended to include such copolymers and blends, as well as the preferred homopolymers of vinylidene difluoride. In a preferred embodiment, the outermost polyvinylidene difluoride layer which is cast upon the porous support is a polyvinylidene difluoride solution containing from 2-22% (wt/vol) polyvinylidene difluoride, more preferably a 5-12% (wt/vol) polyvinylidene difluoride solution.

The membranes of the instant invention are readily prepared with pore opening diameters of 1 µm or smaller and preferably 0.2 µm or smaller, especially 0.12 µm or smaller. Preferably, the density of the surface pore openings having a diameter greater than 0.01 µm and up to about 0.2 µm is equal to or greater than $1 \times 10^5$ pores/cm$^2$, and more preferably greater than $1 \times 10^5$ pores/cm$^2$. In general, pore densities up to about $1 \times 10^{10}$ pores/cm$^2$ or more can be achieved while maintaining satisfactory integrity and mechanical strength, especially for smaller average pore diameters.

The present invention provides uniform and reproducible PVDF microporous membranes with the special surface characteristics of smoothness and multiplicity of rounded, discrete submicron diameter pore openings which include diameters greater than about 0.01 µm. Reverse osmosis membranes typically have pore diameters of less than 0.011 µm. The special surface characteristics of the membranes of the present invention have particular importance in two areas of application, namely, filtration and particle capture. In a filtration operation, a membrane having a spongy surface traps the retained material and consequently becomes clogged. As a result of particle entrapment, there is little prospect of either cleaning the membrane for further use or effectively retrieving the entrapped material.

By contrast, the invention membranes with a smooth surface and discrete pore openings are much less likely to entrap filtered material within the pores. With the invention membrane, the particles tend to collect on the surface of the membrane. When a plaque of retained material has formed on the surface and covers the pores, the accumulated material can readily be removed by a "backwash", wherein solution is forced through from the other (i.e., support) side of the membrane. Consequently, the rinsed membrane can be reused.

The special surface characteristics of smoothness and multiplicity of discrete pore openings having submicron diameters also renders the membranes of the present invention especially applicable to methods of particle capture for analysis. Because the particles collect on the smooth surface they can be directly examined with a microscope. In such an application, the membranes are useful as collectors for direct bacteria counting, for examining phytoplankton, asbestos fibers, virus particles or contaminating particles in water or air, and the like. The invention membranes can also be used in virus absorption and elution assays or for growing colonies of bacteria. The membranes of the instant invention are readily prepared with pore opening diameters of, for example, 0.1 µm, or less, which renders them well suited for such applications.

Another important feature of the membranes of the present invention is that the discrete pores are primarily merely a surface feature. The pore openings connect directly to a subsurface network of interconnected pores which are several fold larger than the surface openings. In effect, flow resistance in the membranes occurs principally at the surface of the membrane.

In applications involving the filtration of aqueous liquids, the hydrophobicity of the instant membranes can be overcome by first equilibrating the membrane with a water miscible organic liquid such as ethanol and then replacing the liquid with aqueous media. In an alternate method, the hydrophobicity of the membrane can be altered by treating the membrane with a hydrophilic agent.

Hydrogels are particularly useful materials for altering the hydrophobicity of the instant membranes. Hydrogels are polymeric materials that are not soluble in water but which are capable of retaining a significant amount of water. Examples of hydrogels which can be used to treat the membranes of the present invention include, but are not limited to, crosslinked polymers of vinyl alcohol, N-vinyl-2-pyrrolidone, acrylamide, methacrylates and hydroxyalkylmethacrylate. Poly(2- hydroxyethylmethacrylate) (PHEMA), is a preferred hydrogel in the treatment of the membranes of the instant invention.

PHEMA is a physically fragile, non-toxic polymer material which exhibits a large degree of compatibility with tissue and body fluids in vivo. An important property of PHEMA hydrogel useful in filtration applications is its permeability only to molecules of molecular weight less than about 8,000, including antibiotics, steroids and tumoricidal drugs, for instance.

Treatment of the membranes of the present invention with PHEMA results in the retention of PHEMA firmly within the structure of the membranes, with consequent effects on membrane permeability. At a level of impregnation with PHEMA such as that provided by a solution of PHEMA less than about 2.5% (wt/vol) the PVDF membrane becomes less hydrophobic to hydrophilic, whereas at higher levels of impregnation, i.e. with solutions of PHEMA greater than about 3.0%, the permeability properties of the membrane reflect those of PHEMA, i.e. hydrophilic but impermeable to substances of molecular weight greater than about 8000.

The present membranes can be impregnated with PHEMA solution in alcohol, preferably 95% ethanol, 5% water. The following methods of impregnation have been found to be convenient.

In one method, the PVDF membrane is immersed in the hydrogel solution, permeated with it, withdrawn and dried at ambient temperature. The amount of time for immersion can be as little as 10 seconds for example, and as long as up to 2 minutes, depending on the thickness of the membrane. Such membranes when impregnated with PHEMA solutions more concentrated than 3% (wt/vol) are distinctly brittle when dry. To avoid such brittleness, instead of air drying, the hydrogel solution treated membrane may be immediately submerged in water for about 5 minutes which serves to desolvate the hydrogel within the pores and results in membranes that are not brittle when dry.

The permeability properties of impregnated PVDF membranes are dependent upon the degree of impregnation with hydrogel. Using PHEMA concentrations greater than about 3% results in membranes having the permeability properties of PHEMA due to a high incorporation of PHEMA, whereas using an immersion solution containing less than about 2.5% PHEMA merely renders the previously hydrophobic PVDF membrane less hydrophobic to hydrophilic.

For example, membranes treated with 2% PHEMA solution are permeable to a substantial fraction of serum proteins, whereas the membranes treated with 4% PHEMA solution exhibit only a slight permeability to serum proteins. The altered permeability to serum proteins is consistent with PHEMA's permeability to molecules smaller than about 8000 molecular weight and impermeability to molecules of molecular weight larger than about 10,000, especially of molecular weight larger than about 20,000. For membranes to exhibit hydrophilic properties, the preferred impregnating solution contains at least 0.1% (wt/vol) poly(2-hydroxyethylmethacrylate). Membranes having the permeability properties of PHEMA are preferably made by immersion in solution comprising at least about 2.5%, and preferably 3% or more PHEMA.

The permeability properties of the PHEMA impregnated PVDF membranes are controlled by the PVDF membrane structure as well as by the degree of impregnation. Expression of the permeability properties of PHEMA is dependent upon the special surface features of the PVDF membranes of the present invention. For example, PVDF membranes made by a process outside the present invention, such as wherein the PVDF solution is gelled in 60% methanol rather than in water or a highly aqueous solution have a spongy PVDF surface structure as revealed by scanning electron microscopy examination and are readily permeable to serum proteins even when impregnated with up to 12% PHEMA solution.

An obvious benefit of the instant membranes is that lamination reinforces the PVDF membrane. Consequently, these membranes can be manufactured with a very thin PVDF layer cast upon a support. Thus, physically stronger and thinner PVDF membranes can be produced by the process of the present invention. Another benefit of the instant membranes is that microporous structures can be produced having the physical, chemical and structural properties of PVDF membranes at one surface and the properties of the support at the other surface. Such PVDF laminates can be useful as a wound dressing, for example. A laminate comprising a hydrophilic support and a hydrophobic outer PVDF layer would be absorptive at the hydrophilic surface adjacent to the wound and protective at the outer hydrophobic surface with submicron pore openings, while permitting access of air to the wound. Alternatively, the hydrophobic PVDF layer can be rendered hydrophilic but permselective as described above to be impermeable to bacteria, viruses, and the like.

The preparation of microporous PVDF membranes in accordance with the process of the present invention and the usefulness of such membranes is demonstrated by the following examples, however, these examples are given only for purposes of illustration and are not meant to be limiting.

EXAMPLE 1

A hydrophilic glass fiber membrane (Gelman Sciences) having 1 $\mu$m diameter pores was clamped at the edges with a metal frame upon a solid glass plate and held in a horizontal position. PVDF powder, Kynar grade 301 (Penwalt Corp.), was dissolved in DEAA at a concentration of 12 g PVDF in 100 ml DEAA. The solution was applied as a 0.03 ml/cm$^2$ layer equivalent to 3.6 mg PVDF/cm$^2$ to the surface of the glass membrane at 23-26° C. Within one minute of application the membrane was submerged in 23-26° C. water. After 20 minutes the water was gently agitated for about 1 minute and this procedure was repeated 3 times for a total submersion time of 80 minutes, after which the membrane was withdrawn, rinsed with clean water, air dried, annealed at 100°C. for about 2 minutes in a water bath and removed from the frame. The product membrane was a laminate, hydrophilic on the support surface and hydrophobic on the PVDF side, with the two surfaces firmly bonded.

The pores on the glass surface of the laminate remained unchanged. The pore openings on the PVDF side, as shown by scanning electron microscopy (SEM) examination at 30,000$\times$magnification had a maximum diameter of about 0.09 $\mu$m. The density of pore openings with diameters in the range of 0.03-0.09 $\mu$m was about $1.4 \times 10^9$/cm$^2$.

The laminate was permeable and chemically resistant to organic liquids such as ethanol, benzene and chloroform. It was also chemically resistant to aqueous solutions such a two molar solutions of ammonia, sulfuric acid, phosphoric acid and hydrochloric acid. The laminate was readily made permeable to aqueous solutions by first impregnating the membrane with a water miscible organic liquid such as ethanol and then immersing it in water or an aqueous solution to replace the organic liquid within the pores. The water loaded membrane was not permeable to microorganisms such as bacteria but was permeable to aqueous solutions of high molecular weight organic solutes, such as proteins. The permeability of the membrane was characterized in the following tests.

The water-loaded membrane was mounted so as to separate a volume of pH 7.3 PBS (buffered physiological saline, 0.02 molar with respect to phosphate) on the glass side of the membrane from a volume of the same PBS on the PVDF side of the membrane but containing 5 mg/ml of one of the following solutes: (a) aprotinin, mol wt 6,500, (b) dextran sulfate, mol wt 8,000, (c) cytochrome C, mol wt 12,200, (d) gamma globulin, mol wt 150,000, (e) thyroglobulin, mol wt 640,000. A differential pressure of 0.5 psi was applied to the chamber containing the solutes. The liquids in both chambers were constantly and gently agitated.

After the initial 2 hours at 25° C., the volume of liquid transported to the PBS chamber, in ml/hr/10 cm$^2$ of membrane surface for each of the solutions was determined to be (a) 11.0, (b) 9.0, (c) 10.0, (d) 8.5 and (e) 7.5. The volumes transmitted through the membrane carried the following concentrations of the respective solutes in mg/ml: (a) 3.1, (b) 4.1, (c) 3.2, (d) 1.9, and (e) 1.4. Both the volume of liquid and the concentration of protein solute transported across the membrane appears to be inversely related to the molecular weight of the proteins tested indicating that the membrane is capable of fractionating a mixture of proteins.

When microorganisms or other particulates are present in the solution to be filtered, they tend to accumulate on the membrane surface during filtration where they can be readily swept off rather than lodge in the pores and foul the membrane.

Because the PVDF side of the laminate membrane is permeable to high molecular weight proteins but is impermeable to microorganisms, has a PVDF surface that will not enmesh microorganisms, and is biologically and chemically inert, the membrane is useful in the recovery of cell products from cell cultures, or in harvesting cells. Cell products include for example, but are not limited to hormones, antibiotics, enzymes, antibodies and therapeutic proteins.

EXAMPLE 2

A laminate membrane was formed as described in Example 1 but with the following changes:

(a) the PVDF was dissolved in DMAA at 5 g/100 ml and the solution was cooled to 8-13° C. prior to use in order to increase its viscosity;

(b) Whatman grade 5 filter paper was used as the support layer;

(c) the layer of PVDF solution applied to the filter paper was about 0.045 ml/cm$^2$ equivalent to 2.25 mg of PVDF/cm$^2$ of the filter paper surface; and (d) the laminate was used without annealing.

Maximum diameter of pore openings at the PVDF surface was 0.09 μm, and the density of pore openings with diameter in the range of 0.03-0.09 μm was $1.1 \times 10^9$ pores/cm$^2$.

The permeability of this laminate membrane for high molecular weight organic solutes was tested in the same manner as in Example 1, and using t he same aqueous solutions of (a) aprotinin, (b) dextran sulfate, (c) cytochrome C, (d) gamma globulin, and (e) thyroglobulin.

After the initial 2 hours at 25° C., the volume of liquid transported to the PBS chamber, in ml/hr/10 cm$^2$ of membrane surface for each of the solutions was: (a) 19.0, (b) 19.5, (c) 21.0, (d) 14.0 and (e) 12.0, respectively. The volumes transmitted through the membrane carried the following concentrations of the respective solutes in mg/ml (a) 3.8, (b) (c) 3.6, (d) 2.3 and (e) 1.8.

In reducing the PVDF layer from 3.6 to 2.25 mg/cm$^2$ the average liquid flow rate through the membranes increased by more than 80%. The average transport of the solutes per unit volume of transported liquid increased from 63% to 72% (of the maximum possible) for the lower molecular weight solutes and from 33% to 38% for the higher molecular weight solutes. Similar results are obtained when the microporous glass filter of Example 1 is substituted for the filter paper support, indicating that transport is controlled by the PVDF layer of the composite membrane.

EXAMPLE 3

Membranes prepared as in Example I were immersed for 4 hours in a solution of PHEMA (Interferon Sciences, Inc., New Brunswick, NJ) in 95% ethanol/water mixture wherein PHEMA (wt/vol) was (A) 1%, (B) 3.6%, or (C) 8%. Excess solution was shaken off and the membranes were immediately submerged in water for 20 minutes and then dried at 25° C.

The PHEMA-impregnated membranes were rendered hydrophilic by the impregnation. Their permeability to high molecular weight organic solutes was tested as described in Example 1 and outlined again below. The membranes were mounted so as to separate a volume of pH 7.3 PBS (phosphate buffered physiological saline, 0.02 molar with respect to phosphate) on the microporous glass side of the membrane from a volume of the same PBS on the PVDF side of the membrane but containing 5 mg/ml of one of the following solutes: (a) aprotinin, mol wt 6,500, (b) dextran sulfate, mol wt 8,000 (c) cytochrome C, mol wt 12,200, (d) gamma globulin, mol wt 150,000, (e) thyroglobulin, mol wt 640,000. A differential pressure of 0.5 psi was applied to the chamber containing the solutes. The liquids in both chambers were constantly and gently agitated.

After the initial 2 hours at 25° C., the volume of liquid transported to the PBS chamber, in ml/hr/10 cm2 of the 1% PHEMA-treated membrane, was 8.5, 9.5, 9.0, 6.5 and 5.0 for solutions (a), (b), (c), (d) and (e) respectively. With the 3.6% PHEMA-treated membrane these volumes were 5.5, 7.0, 8.0, 8.5 and 8.5 and with the 8% PHEMA-treated membrane these volumes were 4.0, 6.0, 7.5, 7.5 and 8.0. The volumes transmitted through the 1% PHEMA membrane carried the following concentrations of the respective solutes in mg/ml: (a) 2.5, (b) 2.7, (c) 2.1, (d) 0.6, and (e) 0.3. The corresponding values for the 3.6% PHEMA membrane were: (a) 2.1, (b) 1.4, (c) none, (d) none, (e) none. The corresponding values for the 8% PHEMA membrane were: (a) 1.9, (b) 1.1, (c) none, (d) none, (e) none.

Membrane laminates fabricated by gelling the PVDF in alcohols as in Comparative Example 1, when treated with PHEMA solutions, at any concentration in the range 0.25 to 8% are permeable to all of the solutes listed above with no indication of a molecular weight cut off or a significant capacity to fractionate a mixture of these solutes. Therefore, only membranes of this invention provided a PVDF structure capable of supporting PHEMA in a manner so as to impart to the structure the ability to fractionate solutes and also establish a permeability limit of about 8,000 Daltons. Furthermore, the surface morphology of the PHEMA impregnated PVDF membranes is not altered and the surface does not entrap or damage filtered microorganisms.

The membrane treated with 1% PHEMA was shown to be substantially permeable to aqueous solutes of molecular weights up to at least 640,000. Furthermore, permeability rates indicated that this membrane can fractionate mixtures of these solutes. Since this membrane is not permeable to microorganisms it is therefore useful not only in harvesting products of cell cultures but possibly also in fractionating these products.

By contrast, membranes treated with solutions comprising at least 3.6% PHEMA were permeable only to solutes with molecular weights 8,000 daltons or smaller. Since enzymes have molecular weights greater than 8,000 daltons, these membranes are particularly useful in enzymatic bioreactors where the molecular weight of the product is less than 8,000 daltons. The product can diffuse through the membrane which confines the enzyme. Another advantage of the PHEMA treated membranes as components of bioreactors, is that PHEMA reduces the adsorptivity of the membrane for proteins, and thereby reduces loss of reaction products in the membrane. Furthermore, the membranes can be sterilized by autoclaving or by steam, and the membrane materials are not subject to biological attack.

EXAMPLE 4

Poly(tetrafluoroethylene) (PTFE) membrane (Zefluor, Gelman Sciences), having a pore diameter of 2 $\mu$m, was clamped at the edges in a horizontal position in a holder. PVDF powder, grade Kynar 401 (Pennwalt Corp.), was dissolved in DMF, 9 g/100 ml. A layer of the solution 0.05 ml/cm$^2$ equivalent to 4.5 mg PVDF/cm$^2$ was spread at 20-23° C. on the surface of the PTFE membrane. Five minutes following the application, the PVDF solution was gelled by submerging the assembly in water at 20-23° C. for 90 minutes with gentle agitation for one minute every thirty minutes. The assembly was withdrawn from the gelling medium, rinsed well in fresh water, dried at ambient temperature, the laminate structure annealed as described in Example 1 and the product membrane, a firmly bonded porous laminate, was dismounted from the holder. The PVDF surface was similar to that described in Example 1 except that the maximum diameter of the pore openings was 0.07 $\mu$m and the density of the pore openings with diameter in the range of 0.03-0.07 $\mu$m was 7.3 $\times$ 10$^9$ pores/cm$^2$. This laminate was composed of two highly hydrophobic microporous layers, wherein both surface materials are highly chemically and biologically resistant and wherein the PVDF surface had discrete, clearly defined pore openings.

The membrane was used to collect particulate materials carried by corrosive gases for analysis. The smooth PVDF surface having small pore openings retained particulates upon its surface and not within the pores, which allowed for examination of the particulates by optical or electron microscopy. Also, because the composite membrane was highly hydrophobic, it did not become clogged by moisture during use.

EXAMPLE 5

Nylon 66 membrane (PALL Corp.) having a 0.65 $\mu$m pore size, was placed in a holder as in the previous examples. PVDF powder, grade Kynar 201 (Penwalt Corp.), was dissolved (7 g/100 ml) in a solvent mixture of 15% DMSO and 85% DMAA (vol/vol). A layer of the solution, 0.06 ml/cm$^2$, equivalent to 4.2 mg PVDF/cm$^2$ was applied to the horizontally held nylon membrane and within 0.5 to 1.0 minute of application the assembly was submerged in 10-15° C. water. Every 30 minutes the water was gently agitated for about one minute and the assembly was withdrawn after 150 minutes, air dried and annealed at 90° C. for about 10 minutes. The product laminate was dismounted from the holder. The PVDF surface was hydrophobic, the nylon surface hydrophilic. The character of the PVDF surface was the same as that in Example I, except that the maximum pore opening diameter was 0.08 $\mu$m and the density of pore openings in the diameter range of 0.03-0.08 $\mu$m was 3 $\times$ 10$^9$ pores/cm$^2$.

The laminate membrane was immersed for 4 hours in a solution of PHEMA in 95% ethanol/water wherein the concentration of PHEMA (wt/vol) was 8%. Excess solution was shaken off and the membrane was immediately submerged in water for 20 minutes and then dried at 25° C.. The membrane was hydrophilic and impermeable to solutes of molecular weight greater than 8,500.

By impregnating the PVDF laminate with PHEMA as described, the following features are achieved: the membrane exhibits the hydrophilic and absorptive capacities of PHEMA but in contrast to self-supporting PHEMA membranes, it is pliable and structurally strong when dry or wet; it functions not only as a barrier to bacteria and viruses but also to substances with molecular weight greater than about 8,500; it is biocompatible; it can be sterilized by steam, autoclaving or by gamma irradiation. Such laminate can be used as a wound dressing wherein the nylon surface in contact with the wound is capable of absorbing excess fluids quickly while the PVDF surface protects the wound from infection. The dressing is readily maintained moist when required by periodic contact with water, and medications having molecular weight less than 8,000 can be transported to the wound through the dressing.

EXAMPLE 6

A laminate membrane was formed as in Example 1, but with the following changes:
(a) the solvent for the PVDF was DMAA (dimethyl acetamide); and
(b) the gelling medium was a 10% (vol) aqueous solution of isopropanol.
Maximum diameter of the pore openings at the PVDF surface was 0.11 $\mu$m, and the density of pore openings with diameter 0.03 $\mu$m or greater was 6.5 $\times$ 10$^9$ pores/cm$^2$. The scanning electron micrograph of the PVDF surface is shown in FIG. 1. This example demonstrates that the aqueous gelling media can include small amounts of alcohol and still achieve the objectives of this invention.

COMPARATIVE EXAMPLE 1

Laminate membranes were prepared by the procedure of Example 6 except that the gelling medium was methanol. By contrast with the product of Example 6 where the PVDF surface examined by SEM at 20,000×magnification (FIG. 1) appeared as a solid continuum with discrete pore openings, this PVDF surface resembled a fused tangle of strands of the polymer material (FIG. 2).

In this type of tortuous surface structure the boundaries of the pore openings are not clearly defined and so the diameter of these pore openings is only roughly approximated, ranging, as seen for example in FIG. 2, from 0.2 μm to 1.1 μm, with most of the pores having an apparent diameter greater than 0.5 μm.

In Examples 1 and 2 the membranes exhibited an ability for partially fractionating proteins by molecular weight. Membranes made by using alcohol as a gelling medium, as in this Example, do not have this ability.

Cells and microorganisms can be damaged during filtration when straddling the strands of the tortuous PVDF surface structure of the membrane of this example. Furthermore, cells, microorganisms and other particulates are more readily entrapped in the PVDF surface of such a membrane than in the membranes of Examples 1, 2 or 4, resulting in much more rapid and irreversible fouling of the membrane, i.e., fouling that cannot be effectively remedied by backwashing.

As a result of the above deficiencies, the membranes of this example are not fully suitable for harvesting cells and microorganisms nor are they suitable for collecting particulates for analysis. Also, these membranes, in contrast to those described in Examples 2 and 5, do not acquire the important permeability properties when impregnated with the PHEMA hydrogel.

What is claimed is:

1. A microporous composite membrane which comprises at least two layers laminated in series wherein one of the layers is a porous support layer and the adjacent layer comprises at least 90% polyvinylidene difluoride and the exposed polyvinylidene difluoride surface of the membrane has discrete pore openings wherein at least 90% of the pore openings have diameters smaller than about 0.2 micron, and the density of pore openings having a diameter greater than about 0.1 micron and smaller than about 0.2 micron is at least $1 \times 10^5$ pores/cm$^2$, said composite membrane further comprising a hydrophilic agent within the pores of the polyvinylidene difluoride layer which is crosslinked polymer of hydroxyalkyl methacrylate, said composite membrane being permeable to substances in aqueous solution with molecular weights smaller than 8,000, but impermeable to substances with molecular weights greater than about 20,000.

2. The microporous composite membrane of claim 1, wherein the support comprises a hydrophilic material.

3. The microporous composite membrane of claim 1, wherein the support comprises a hydrophobic material.

4. The microporous composite membrane of claim 1 wherein at the exposed polyvinylidene difluoride surface at least 90% of pore openings have diameters smaller than 0.12 μm.

5. The microporous composite membrane of claim 1 wherein the hydrophilic agent is poly(2-hydroxyethylmethacrylate) and said membrane is permeable to substances in aqueous solution with molecular weights smaller than about 8,000 but impermeable to substances with molecular weights greater than about 10,000.

6. The microporous composite membrane of claim 1 wherein the supporting membrane comprises a material selected from the group consisting of natural polymers, synthetic polymers, carbon, metals, metal alloys, ceramics, glass and mixtures thereof.

7. The microporous composite membrane of claim 1 wherein the surface of the support layer onto which the polyvinylidene difluoride is cast has pore openings wherein at least 80% of the pores have a diameter in the range of from 0.01 μm to 25 μm.

8. The microporous composite membrane of claim 7 wherein at least 80% of the pores of the support layer have a diameter in the range of from 0.01 μm to 2 μm.

9. The microporous composite membrane of claim 1, wherein the density of pore openings having a diameter greater than 0.01 μm and smaller than 0.2 μm is at least $1 \times 10^8$ pores/cm$^2$.

10. The microporous composite membrane of claim 1 wherein the polyvinylidene difluoride layer comprises 0.5-20 mg polyvinylidene difluoride per cm$^2$ of membrane surface.

11. The microporous composite membrane of claim 10 wherein the polyvinylidene difluoride layer comprises from 1 to 10 mg polyvinylidene difluoride per cm$^2$ of membrane surface.

12. A process for separating at least one component from a mixture of components in a liquid medium which comprises contacting one surface of the microporous composite membrane of claim 8 with said mixture of components in liquid medium and applying a driving force across said membrane, whereby said at least one component either selectively passes through the membrane or is selectively prevented by the membrane from passing through it.

13. The process of claim 12 wherein the driving force comprises applying a higher pressure to the liquid medium which contacts one surface of the membrane than the pressure which is exerted upon the opposite surface of said membrane.

14. The process of claim 12 wherein the driving force comprises applying an electric current across the membrane.

15. The process of claim 12 wherein the liquid medium contacts the polyvinylidene difluoride surface of the composite membrane.

16. A process for filtering particulate material from a gaseous medium which comprises contacting the polyvinylidene difluoride surface of the microporous composite membrane of claim 1 with said medium and applying a driving force across said membrane, whereby the gaseous medium passes through said membrane and particulate material is collected on the polyvinylidene difluoride surface of the membrane.

17. A wound dressing comprising the microporous composite membrane of claim 1 wherein said porous support layer comprises a hydrophilic material and is adapted to contact the wound.

18. A process for preparing a microporous composite membrane comprising at least two layers laminated in series wherein one of the layers is a porous support layer and the adjacent layer comprises at least 90% polyvinylidene difluoride and has at the exposed polyvinylidene difluoride surface discrete pore openings wherein at least 90% of the pore openings have a diameter smaller than 0.2 microns, said process comprising casting on the surface of the support a solution of polyvinylidene difluoride in a water miscible solvent, contacting said cast solution with an aqueous medium to cause said polyvinylidene difluoride to gel upon said support and drying to form said composite membrane, and thereafter treating the laminated membrane by immersion of the membrane in an impregnating solution of a hydrophilic agent in a solvent, followed by immersion in water to desolvate the hydrophilic agent in the membrane, said hydrophilic agent being poly (2-hydroxyethyl methacrylate).

19. The process of claim 18 wherein the exposed polyvinylidene difluoride surface has a pore density of pores with pore openings in the range of from about 0.01 to about 0.2 μm of at least $1 \times 10^5$ pores/cm$^2$.

20. The process of claim 19 wherein at least 90% of the pore openings have diameters smaller than 0.12 μm.

21. The process of claim 20 wherein the aqueous medium is selected from the group consisting of water, aqueous solutions of inorganic salts, aqueous solutions of organic salts and aqueous solutions of water-soluble organic solvents.

22. The process of claim 20 wherein the aqueous gelling medium is water or an aqueous solution of water-soluble organic solvents and the weight percent of water in said aqueous solution is at least 65%.

23. The process of claim 20 wherein the polyvinylidene difluoride solution contains from 2–22% (wt/vol) polyvinylidene difluoride.

24. The process of claim 23 wherein the polyvinylidene difluoride solution contains 5–12% (wt/vol) polyvinylidene difluoride.

25. The process of claim 20 wherein the polyvinylidene difluoride solvent is selected from the group consisting of dimethyl formamide, dimethyl acetamide, diethyl acetamide, dimethyl sulfoxide, mixtures thereof.

26. The process of claim 20 wherein the solvent is dimethylacetamide.

27. The process of claim 20 which further comprises partly evaporating the solvent in which polyvinylidene difluoride is dissolved prior to gelling the polyvinylidene difluoride solution upon the surface of the support membrane by immersion in aqueous media.

28. The process of claim 20 which further comprises annealing the laminated membrane for at least one minute at 70 to 100° C.

29. The process of claim 18 wherein the solvent for the hydrophilic agent comprises about 95% ethanol and about 5% water.

30. The process of claim 18 wherein the concentration of poly(2-hydroxyethyl methacrylate) in the impregnating solution is at least about 0.1% (wt/vol).

31. The process of claim 18 wherein the concentration of poly(2-hydroxyethyl methacrylate) in the impregnating solution is at least about 2.5% (wt/vol).

* * * * *